United States Patent
He et al.

(10) Patent No.: US 10,363,164 B2
(45) Date of Patent: Jul. 30, 2019

(54) TOOL AND TOOL SYSTEM HAVING INDEPENDENT AXIAL AND TRANSVERSE FORCE SENSING

(71) Applicant: The Johns Hopkins University, Baltimore, MD (US)

(72) Inventors: Xingchi He, Columbia, MD (US); Iulian Iordachita, Lutherville-Timonium, MD (US); Russell H. Taylor, Severna Park, MD (US); James T. Handa, Baltimore, MD (US); Peter L. Gehlbach, Monkton, MD (US)

(73) Assignee: The Johns Hopkins University, Baltimore, MD (US)

( * ) Notice: Subject to any disclaimer, the term of this patent is extended or adjusted under 35 U.S.C. 154(b) by 134 days.

(21) Appl. No.: 15/234,896

(22) Filed: Aug. 11, 2016

(65) Prior Publication Data
US 2017/0156928 A1 Jun. 8, 2017

Related U.S. Application Data

(60) Provisional application No. 62/203,746, filed on Aug. 11, 2015.

(51) Int. Cl.
*A61F 9/007* (2006.01)
*A61B 34/30* (2016.01)
(Continued)

(52) U.S. Cl.
CPC .......... *A61F 9/00727* (2013.01); *A61B 34/30* (2016.02); *A61F 9/007* (2013.01);
(Continued)

(58) Field of Classification Search
CPC .... A61F 9/00727; A61F 9/007; A61F 9/0017; B25J 9/023; B25J 13/085; G01L 1/246;
(Continued)

(56) References Cited

U.S. PATENT DOCUMENTS

| 2007/0151390 A1* | 7/2007 | Blumenkranz .... A61B 19/2203 74/490.06 |
| 2013/0053730 A1* | 2/2013 | Kotlanka .......... A61M 25/0068 600/585 |

(Continued)

OTHER PUBLICATIONS

Balicki et al., "Micro-force sensing in robot assisted membrane peeling for vitreoretinal surgery," in International Conference on Medical Image Computing and Computer Assisted Intervention, vol. 13, Jan. 2010, pp. 303-310.
(Continued)

*Primary Examiner* — Thanh Luu
*Assistant Examiner* — Jennifer D Bennett
(74) *Attorney, Agent, or Firm* — Venable LLP; Henry J Daley

(57) ABSTRACT

A force-sensing tool includes a tool shaft that has a proximal end and a distal end, a flexure section attached at a first end to the distal end of the tool shaft, a tool tip operatively connected to the flexure section such that axial forces applied to the tool tip are coupled primarily to a first portion of the flexure section and transverse forces applied to the tool tip are coupled primarily to a second portion of the flexure section, an axial force sensor coupled to the first portion of the flexure section, and a transverse force sensor coupled to the second portion of the flexure section. The axial force sensor responds to axial forces applied to the tool tip substantially independently of the transverse forces applied to the tool tip under a designed operating range of forces, and the transverse force sensor responds to transverse
(Continued)

forces applied to the tool tip substantially independently of the axial forces applied to the tool tip under the designed operating range of forces.

17 Claims, 10 Drawing Sheets
(1 of 10 Drawing Sheet(s) Filed in Color)

(51) Int. Cl.
| | |
|---|---|
| A61F 9/00 | (2006.01) |
| B25J 9/02 | (2006.01) |
| B25J 13/08 | (2006.01) |
| G01L 1/24 | (2006.01) |
| A61B 34/20 | (2016.01) |
| A61B 90/00 | (2016.01) |

(52) U.S. Cl.
CPC ............ *A61F 9/0017* (2013.01); *B25J 9/023* (2013.01); *B25J 13/085* (2013.01); *G01L 1/246* (2013.01); *A61B 2034/2051* (2016.02); *A61B 2090/064* (2016.02)

(58) Field of Classification Search
CPC ............... G01L 5/166; A61B 2090/064; A61B 2090/065; A61B 2090/066; A61B 34/30
See application file for complete search history.

(56) References Cited

U.S. PATENT DOCUMENTS

| | | | |
|---|---|---|---|
| 2013/0190734 A1* | 7/2013 | Taylor | A61F 9/007 606/1 |
| 2015/0075250 A1* | 3/2015 | Kosa | G01L 5/162 73/1.15 |
| 2015/0272443 A1* | 10/2015 | Sliwa | A61B 5/0084 600/478 |

OTHER PUBLICATIONS

Gonenc et al., "Design of 3-DOF force sensing micro-forceps for robot assisted vitre-oretinal surgery," in International Conference of the IEEE Engineering in Medicine and Biology Society, vol. 2013, Jan. 2013, pp. 5686-5689.
He et al., "A novel dual force sensing instrument with cooperative robotic assistant for vitreoretinal surgery," in IEEE International Conference on Robotics and Automation, 2013, pp. 213-218.
He et al., "A sub-millimetric 3-DOF force sensing instrument with integrated fiber Bragg grating for retinal microsurgery," IEEE Transactions on Biomedical Engineering, vol. 61, No. 2, 2014, pp. 522-534.
Jagtap et al., "Applied force during vitreoretinal microsurgery with handheld instruments." in International Conference of the IEEE Engineering in Medicine and Biology Society, vol. 4, No. 1, Jan. 2004, pp. 2771-2773.
Kuru et al., "Force sensing micro-forceps for robot assisted retinal surgery," International Conference of the IEEE Engineering in Medicine and Biology Society, Jan. 2012, pp. 1401-1404.
Park et al., "MEMS tri-axial force sensor with an integrated mechanical stopper for guidewire applications," Microsystem Technologies, vol. 19, No. 7, 2012, pp. 1005-1015.
Peirs et al., "A micro optical force sensor for force feedback during minimally invasive robotic surgery," Sensors and Actuators A: Physical, vol. 115, No. 2-3, pp. 447-455, 2004.
Puangmali et al., "Miniature 3-axis distal Force Sensor for Minimally invasive surgical palpation," IEEE/ASME Transactions on Mechatronics, vol. 17, No. 4, Aug. 2012, pp. 646-656.
Sun et al., "A sub-millimetric, 0.25 mN resolution fully integrated fiber-optic force-sensing tool for retinal microsurgery," International Journal of Computer Assisted Radiology and Surgery, vol. 4, No. 4, Jun. 2009, pp. 383-390.
Uneri et al., "New Steady-Hand Eye Robot with micro-force sensing for vitreoretinal surgery," in IEEE International Conference on Biomedical Robotics and Biomechatronics, 2010, pp. 814-819.
Baki et al., "Design and characterization of a novel, robust, tri-axial force sensor," Sensors and Actuators A: Physical, vol. 192, 2013, pp. 101-110.
Baki et al., "Miniature tri-axial force sensor for feedback in minimally invasive surgery," in IEEE International Conference on Biomedical Robotics and Biomechatronics, 2012, pp. 805-810.
Bell et al., "Integrating optical fiber force sensors into microforceps for ORL microsurgery," in 32nd Annual International Conference of the IEEE Engineering in Medicine and Biology Society, Aug. 2010, pp. 1848-1851.
Berkelman et al., "A miniature instrument tip force sensor for robot/human cooperative microsurgical manipulation with enhanced force feedback," in International Conference on Medical Image Computing and Computer Assisted Intervention, 2000, pp. 247-286.
Gupta et al., "Surgical forces and tactile perception during retinal microsurgery," in International Conference on Medical Image Computing and Computer Assisted Intervention, vol. 1679, 1999, pp. 1218-1225.
He et al., "Force sensing micro-forceps with integrated fiber Bragg grating for vitreoretinal surgery," SPIE Photonics West, vol. 8218, No. 82180W, 2012, pp. 1-7.
He et al., "Toward Clinically Applicable Steady-Hand Eye Robot for Vitreoretinal Surgery," in ASME 2012 International Mechanical Engineering Congress and Exposition, 2012, pp. 145-153.
Liu et al., "Miniature fiber-optic force sensor based on low-coherence Fabry-Perot interferometry for vitreoretinal microsurgery," Biomedical Optics Express, vol. 3, No. 5, May 2012, pp. 1062-1076.
Menciassi et al., "Force feedback-based microinstrument for measuring tissue properties and pulse in microsurgery," in IEEE International Conference on Robotics and Automation, May 2001, pp. 626-631.
Polygerinos et al., "Triaxial catheter-tip Force sensor for MRI-guided cardiac procedures," IEEE/ASME Transactions on Mechatronics, vol. 18, No. 1, Feb. 2013, pp. 386-396.
Seibold et al., "Prototype of instrument for minimally invasive surgery with 6-axis force sensing capability," in IEEE International Conference on Robotics and Automation, Apr. 2005, pp. 496-501.
Valdastri et al., "Integration of a miniaturised triaxial force sensor in a minimally invasive surgical tool," IEEE Transactions on Biomedical Engineering, vol. 53, No. 11, Nov. 2006, pp. 2397-2400.

* cited by examiner

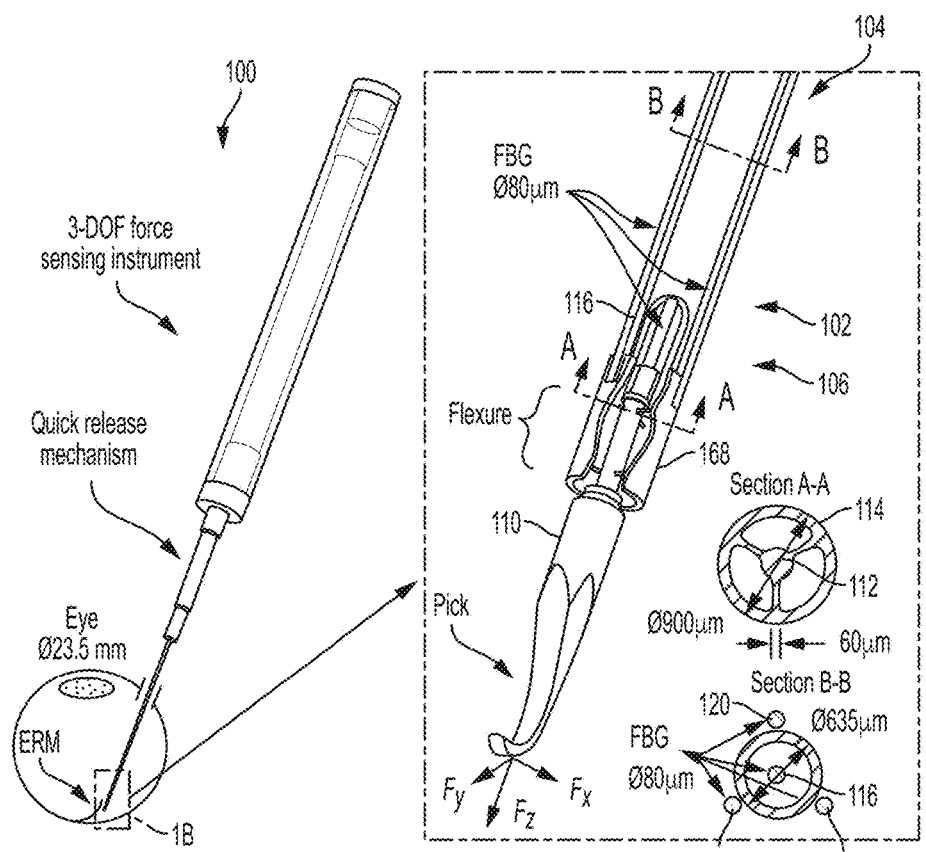
FIG. 1A
FIG. 1B
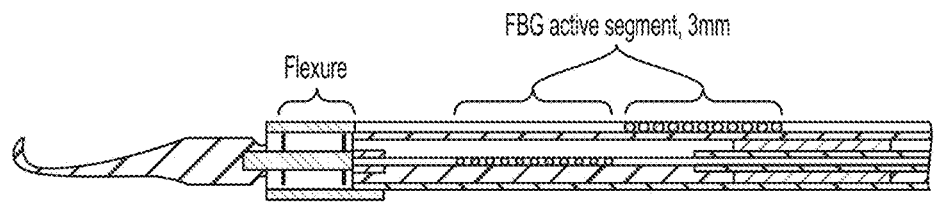
FIG. 1C

TOOL AND TOOL SYSTEM HAVING INDEPENDENT AXIAL AND TRANSVERSE FORCE SENSING

This application claims priority to U.S. Provisional Application No. 62/203,746 filed Aug. 11, 2015, the entire content of which is hereby incorporated by reference.

This invention was made with Government support under grant numbers EB 000526 and EB 007969 awarded by the National Institutes of Health (NIH). The Government has certain rights in the invention.

BACKGROUND

1. Technical Field

The field of the currently claimed embodiments of this invention relates to a tool and tool system, and more particularly to a tool and tool system having independent axial and transverse force sensing.

2. Discussion of Related Art

Retinal microsurgery involves complex intraocular surgical procedures to treat retina-related diseases, e.g., epiretinal membrane (ERM), diabetic retinopathy, retinal detachment, and macular holes. During retinal microsurgery, the surgeon inserts long, thin ophthalmic instruments through trocars on the sclera to perform fine manipulation of the delicate eye tissue in a small constrained space (average axial length of the human eye is about 23.5 mm). One challenge to treatment stems from the microscopic dimensions and the fragility of the tissues in the eye. Another challenge derives from the human physiological limitations, such as surgeon hand tremor and fatigue. One of the most formidable technical challenges is the lack of force sensing. Forces exerted in retinal microsurgery are generally well below the human sensory threshold. A previous study [1] has shown that 75% of forces applied during in vitro retinal manipulation in porcine cadaver eyes are less than 7.5 mN, and only 19% of the events at this force level can be felt by the surgeons. Large forces are undesirable and can potentially damage the delicate retina. Incorporating force sensing capability into the ophthalmic instrument can enable quantitative monitoring of force applied during retinal microsurgery. It can be used to provide awareness of sub-tactile tool-tissue forces to the surgeon. The technology can also be incorporated into robotic systems to provide haptic feedback and motion guidance.

There has been considerable work on force sensing for microsurgery, micromanipulation, and minimally invasive surgery (MIS). Menciassi et al. [2] developed a piezo-actuated microgripper with a dimension of 17×0.5×0.4 mm. The microgripper is instrumented with strain gauges for force sensing to provide haptic feedback in microsurgery. Peirs [3] designed a MIS instrument using intensity modulated optic sensors. It provides triaxial force sensing with a resolution of 0.04 N. Seibold et al. [4] utilized a flexure Steward platform with strain gauges to integrate 6-axis force sensing into an actuated MIS instrument. Polygerinos et al. [5] developed a triaxial catheter-tip force sensor for MRI-guided cardiac ablation procedures. Furthermore, various studies have investigated different force sensing techniques, such as piezoresistive strain gauges [6]-[9] and fiber optical sensors [10], [11]. However, these designs cannot be directly applied to retinal microsurgery due to the specific requirements on the force sensing range (≥10 mN), resolution (≤1 mN), and dimensions (≤0.9 mm in diameter). It is also desired that the force sensor is integrated into the distal portion of the tool shaft, typically located inside the eye. Force sensors mounted in the handle of the microsurgical tool [12] cannot distinguish the force exerted at the tool tip and the contact force at the sclerotomy [13]. Therefore, there remains a need for an improved tool and tool system having independent axial and transverse force sensing.

SUMMARY

A force-sensing tool according to an embodiment of the current invention includes a tool shaft that has a proximal end and a distal end, a flexure section attached at a first end to the distal end of the tool shaft, a tool tip operatively connected to the flexure section such that axial forces applied to the tool tip are coupled primarily to a first portion of the flexure section and transverse forces applied to the tool tip are coupled primarily to a second portion of the flexure section, an axial force sensor coupled to the first portion of the flexure section, and a transverse force sensor coupled to the second portion of the flexure section. The axial force sensor responds to axial forces applied to the tool tip substantially independently of the transverse forces applied to the tool tip under a designed operating range of forces, and the transverse force sensor responds to transverse forces applied to the tool tip substantially independently of the axial forces applied to the tool tip under the designed operating range of forces.

A force-sensing tool system according to an embodiment of the current invention includes a tool force detection system, a force-sensing tool that has force sensors configured to communicate with the tool force detection system, and a processor configured to communicate with the tool force detection system. The force-sensing tool includes a tool shaft that has a proximal end and a distal end, a flexure section attached at a first end to the distal end of the tool shaft, a tool tip operatively connected to the flexure section such that axial forces applied to the tool tip are coupled primarily to a first portion of the flexure section and transverse forces applied to the tool tip are coupled primarily to a second portion of the flexure section, an axial force sensor coupled to the first portion of the flexure section, and a transverse force sensor coupled to the second portion of the flexure section. The axial force sensor responds to axial forces applied to the tool tip substantially independently of the transverse forces applied to the tool tip under a designed operating range of forces, and the transverse force sensor responds to transverse forces applied to the tool tip substantially independently of the axial forces applied to the tool tip under the designed operating range of forces.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further objectives and advantages will become apparent from a consideration of the description, drawings, and examples.

FIGS. 1A-1C provide a CAD model of a 3-DOF force sensing instrument according to an embodiment of the current invention. The tool is used to peel off ERM (a) (FIG. 1A). FIG. 1B shows (b) a close-up view of the tool tip force sensing segment. Part of the tubular tool shaft is removed to reveal the flexure and FBG sensor in the center of the tool shaft. Section A-A is a section view of the flexure. Section B-B shows the configuration of the FBG sensors. FIG. 1C shows a longitudinal section view (c) of the distal force sensing segment. The FBG active segments of the FBG sensors are highlighted with dashed lines.

FIG. 6 shows $\Delta$ and equivalent bending modulus in 360° bending orientation.

DETAILED DESCRIPTION

Figure 1D:
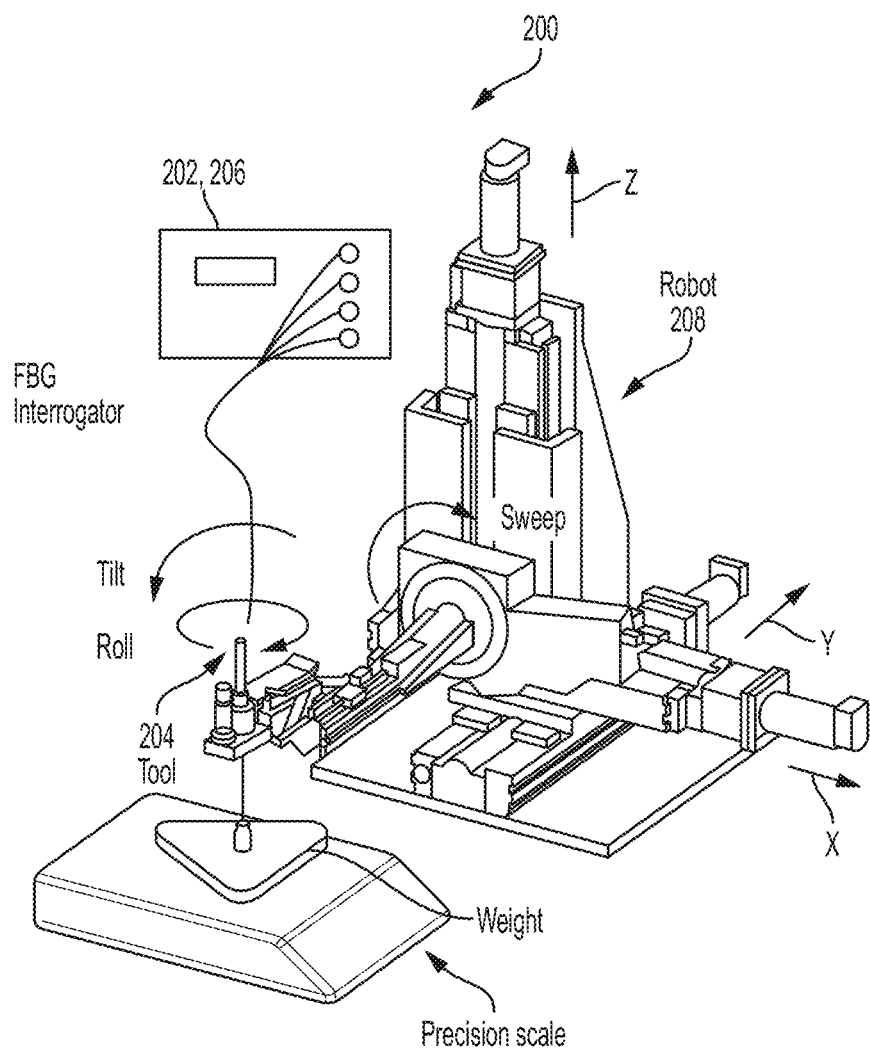
FIG. 1D is a schematic illustration of a force-sensing tool system according to some embodiments of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention are directed to a miniaturized triaxial force sensor that provides decoupled axial and transverse force sensing within a sub-millimeter diameter. However, the general concepts of the invention are intended to extend to embodiments of greater than 1 mm diameter. The general concepts of the current invention are not limited to particular sizes of the tool shaft. The force sensing resolution can be less than 1 mN in the axial direction and less than 0.2 mN in the transverse direction according to some embodiments of the current invention. Due to its small size, this force sensor can be integrated into various interventional tools to enable direct force sensing with very fine force resolution. In some embodiments, the tool can be for micro-manipulation, such as, but not limited to, a micro-pick. However, tools other than micromanipulation tools are intended to be included within the general concepts of the current invention. For example, some embodiments can be directed to interventional and/or diagnostic tools, such as, but not limited to, catheters, biopsy needles, endoscopes, and palpation tools. (See Xingchi He, Peter Gehlbach, James Handa, Russell Taylor, and Iulian Iordachita, "Development of A Miniaturized 3-DOF Force Sensing Instrument for Robotically Assisted Retinal Microsurgery and Preliminary Results," in Proc. IEEE RAS & EMBS International Conference on Biomedical Robotics and Biomechatronics (BioRob) Aug. 12-15, 2014. Sao Paulo, Brazil, pp. 252-258, the entire contents of which are incorporated herein by reference.)

Some embodiments of the current invention can provide the following:

A miniature force sensor integrated into a small interventional tool that can measure 3-dimensional (3D) forces and can include temperature compensation or correction.

This force sensor can have a diameter of 0.9 mm and a length of 8 mm. Its size can be further reduced to 0.63 mm in diameter and 3-5 mm in length. It can enable triaxial force sensing with very fine sensitivity. The force sensing resolution can be less than 1 mN in axial direction and less than 0.2 mN in transverse direction.

This force sensor uses a flexure to decouple axial and transverse force sensing. This flexure also improves the axial force sensing sensitivity with the flexure elasticity. At the same time, this flexure minimizes the axial force sensing noise attributed to transverse forces.

Miniature strain sensors are configured to decouple axial and transverse force sensing. Different modes of the sensor responses are used to calculate axial and transverse forces, in order to improve the independent force sensing performances in axial and transverse directions.

Fiber optic strain sensors can be used in some embodiments, while other strain sensors can be used in further embodiments, such as, but not limited to, strain gauges, piezoelectric sensors, and other optical strain sensors, etc.

Triaxial force sensing ophthalmic tools are shown as an example application. The same force sensing mechanism can be integrated in to other interventional tools such as, but not limited to, catheters, needles, endoscopes, etc.

The triaxial force sensing information can be rendered with auditory cues to provide force feedback to users.

The triaxial force sensing interventional tools can be used with a robotic device to enable force-based robotic assistance and feedback.

FIG. 1A is an illustration of a force-sensing tool 100 according to an embodiment of the current invention. As can be seen more clearly in FIG. 1B, the force-sensing tool 100 has a tool shaft 102 comprising a proximal end 104 and a distal end 106. The force-sensing tool 100 also has a flexure section 108 attached at a first end to the distal end of the tool shaft, and a tool tip 110 operatively connected to the flexure section 108 such that axial forces applied to the tool tip are coupled primarily to a first portion 112 of the flexure section 108 and transverse forces applied to the tool tip are coupled primarily to a second portion 114 of the flexure section 108. An axial force sensor 116 is coupled to the first portion 112 of the flexure section 108. In the embodiment of FIGS. 1B and 1C, the axial force sensor includes the optical fiber shown that runs along the central axis of the force-sensing tool 100. The optical fiber has one or more Fiber Bragg Gratings (FBGs) written therein. However, the general concepts of the current invention are not limited to only sensors using optical fibers with FBGs. The force-sensing tool 100 also has a transverse force sensor (118, 120, 122) coupled to the second portion 114 of the flexure section 108. In this embodiment, the transverse force sensor includes three optical fibers (118, 120, 122) that have FBGs written therein. However, the general concepts of the current invention are not limited to only transverse force sensors that have optical fibers with FBGs.

The axial force sensor 116 responds to axial forces applied to the tool tip 110 substantially independently of the transverse forces applied to the tool tip 110 under a designed operating range of forces. The transverse force sensor (118, 120, 122) responds to transverse forces applied to the tool tip substantially independently of the axial forces applied to the tool tip 110 under the designed operating range of forces. In some embodiments, The force-sensing tool according to claim 1, the optical fiber 116 axial force sensor extends along an inner lumen of the tool shaft 102 such that the first portion 112 of the flexure section 108 and the optical fiber 116 coupled thereto are free to move in an axial direction relative to the second portion 114 of the flexure section 108.

In some embodiments, the transverse force sensor includes a plurality of optical fibers (118, 120, 122), each having a Bragg Grating written therein. The plurality of optical fibers (118, 120, 122) extend from said proximal end 104 to the distal end 106 of the tool shaft 102 and are coupled at a distal end to the second portion 114 of the flexure section 108 to become strained in response to transverse forces applied to the tool tip 110 substantially independently of axial forces applied to the tool tip 110.

The tool tip 110 can be a micro-pick for retinal microsurgery in some embodiments. However; the concepts of the current invention are not limited to the particular type of tool tip 110. A wide range of tool tips are used for micro-surgery and other micromanipulation tasks. These tools can be use according to some embodiments of the current invention.

In some embodiments, the tool shaft 102 can have a diameter that is a maximum of 0.9 mm. However, the general concepts of the current invention are not limited to only that example.

In some embodiments, the designed operating range of forces for the transverse force sensor and the axial force sensor can be from 0 to 40 mN. However, the general concepts of the current invention are not limited to only this range.

FIG. 1D is an illustration of a force-sensing system 200 according to an embodiment of the current invention. The force-sensing system 200 includes a tool force detection system 202, a force-sensing tool 204 that has force sensors configured to communicate with the tool force detection system 202, and a processor 206 configured to communicate with the tool force detection system 202. The force-sensing tool 204 can be an embodiment of the force-sensing tool 100 according to embodiments of the current invention as described in more detail above.

In some embodiments, the force-sensing system 200 can also include a robotic system 208 in which the force-sensing tool 204 is attached to the robotic system 208. The force-sensing system 200 is not limited to only the particular robotic system 208 illustrated in FIG. 1D.

The following examples describe some embodiments in more detail. The broad concepts of the current invention are not intended to be limited to the particular examples. Further, concepts from each example are not limited to that example, but may be combined with other embodiments of the system.

EXAMPLES

Our approach according to some embodiments of the current invention is to integrate fiber optic sensors into the tool shaft, close to the tool tip, such that the sensors are located inside the eye when the tool is used to manipulate the eye tissue. We developed a family of two degrees of freedom (DOF) force sensing tools [14]-[16] that can measure the transverse forces with 0.25 mN resolution. Our previous work has further investigated 3-DOF force sensing instruments using a Fabry-Perot interferometer [17] and fiber Bragg gratings (FBG) [18], [19]. Some embodiments of the current invention are directed to a new design of a sub-millimetric 3-DOF force sensing instrument with integrated FBG sensors. A new flexure is provided to improve the axial force sensing, and reduce crosstalk from the transverse force. The tool design, fabrication, calibration, and experimental results for an example according to an embodiment of the current invention are described in the following sections.

TABLE I

DESIGN SPECIFICATIONS OF THE 3-DOF FORCE SENSING INSTRUMENT

| | |
|---|---|
| Dimension | Tool shaft diameter ≤ 0.9 mm |
| | Tool shaft length ≈ 30 mm |
| | Sensing segment length ≤ 15 mm |
| Sensing performance | Force resolution (X/Y) ≤ 0.25 mN |
| | Force resolution (Z) ≤ 1 mN |
| | Force range (X/Y/Z) ≥ 10 mN |
| | Sampling rate ≥ 100 Hz |
| Additional requirements | Compatible with the tool quick release mechanism of the Steady-Hand Eye Robot |

Design and Fabrication

Retinal microsurgery requires the force sensor to provide high resolution force sensing within strict dimension constraints. To achieve the design specifications, we incorporate high sensitivity FBG sensors with a new flexure design. The force sensor prototype is assembled from components fabricated with photochemical etching and laser micro-machining.

Design Requirements

Table I summarizes the design specifications for the 3-DOF force sensing instrument according to an embodiment of the current invention. In order to achieve accurate sensing of the tool-tissue forces, it is important to design a compact force sensor that fits into the distal end of the tool shaft. The diameter of the force sensor needs to be less than the tool diameter (≤0.9 mm, i.e., 20 Ga). The length of the force sensor should be less than 15 mm to ensure that the force sensor stays inside the eye with sufficient clearance for tool motion.

The desired force range is at least 10 mN because most of the forces exerted during retinal microsurgery are below 7.5 mN in magnitude [1]. Ophthalmic instruments are long and thin, therefore their axial stiffness is significantly higher than the transverse/bending stiffness. The major design challenge is to integrate axial force sensing with high sensitivity. The desired force resolution is 0.25 and 1 mN for transverse and axial forces, respectively. In addition, we want to integrate a tool quick-release mechanism [20] into the tool handle, so that the 3-DOF force sensing tool can be incorporated with the Steady-Hand Eye Robot [20], [21] to enable force feedback and force control methods [21]-[23].

Force Sensor Concept Design

Previous work by our group [19] demonstrated the 3-DOF force sensing capability using FBG sensors with a miniaturized flexure. One drawback of the flexure design presented in [19] is that the flexure increases deformation under both axial and transverse forces. While reducing the structure stiffness under axial force is desired for improving axial force sensing sensitivity, large bending deformation under transverse force can introduce significant crosstalk noise to interfere with axial force sensing. In the previous design, this problem is intended to be mitigated by the FBG sensor configuration: first, the FBG sensor for axial force sensing is aligned with the tool axis in order to minimize the noise from bending; second, the three FBG sensors for transverse force sensing are placed proximal to the flexure so that they are isolated from the flexure deformation. In this iteration, the flexure design is improved to provide maximum deformation under axial force load and minimum deformation under transverse force load. FIGS. 1A-1C illustrate the sensor design concept according to an embodiment of the current invention. Similar to our 2-DOF force sensing tools [14]-[16], three outer FBG sensors are arranged at 120° intervals along the tubular tool shaft, as shown in FIG. 1B. They are used to measure the transverse force. Axial force sensing is realized by combining a flexure and an inner FBG sensor. The flexure consists of an outer tube connected to an inner wire by six thin flexible beams. Each beam is 50 µm thick, 60 µm wide, and 200 µm long. The beams are arranged in two separate planes that are 1 mm longitudinally apart. Within each plane, the three beams form a Y-shape configuration with 120° intervals. The distal end of the inner wire is joined with the micro-pick, while its proximal end is connected to the inner FBG sensor that is aligned with the tool axis. Theoretically, this FBG sensor only measures the strain generated by axial force, decoupled from transverse force, because it should be placed on the bending neutral axis, i.e., the tool axis. However, it is in practice difficult to achieve perfect alignment. The flexure should strengthen the decoupling of axial force sensing from the transverse forces, as well as provide strain amplification under axial force load. All four FBG sensors have a 3 mm FBG active segment with a center Bragg wavelength of 1545 nm (Technica S.A., Beijing, China). The fiber cladding diameter is 80 µm, while the fiber diameter including the coating is 100 µm.

Figures 2A, 2B:
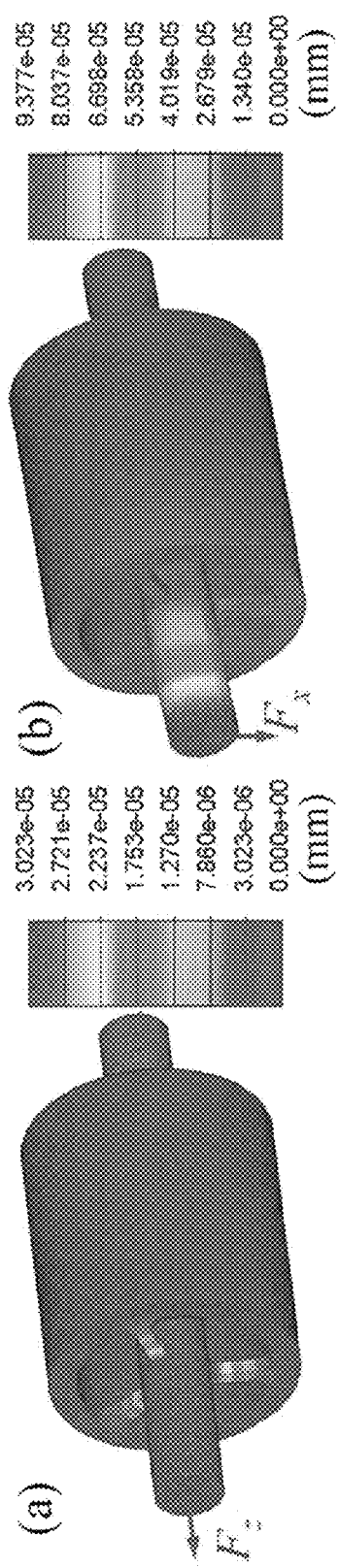
FIGS. 2A-2B show displacement of a flexure according to an embodiment of the current invention under 10 mN axial force (a) and under 10 mN transverse force (b) in a finite element analysis (FEA) simulation. While the displacement is well transferred to the proximal output end under axial force, the displacement is minimized at the output end under transverse force. The material used in the FEA simulation is stainless steel with a Young's modulus of 193 GPa.

Finite element analysis (FEA) is carried out using Creo/Simulate (PTC, Needham, Mass.) to evaluate the flexure behavior under axial and transverse load. FIGS. 2A-2B show the displacement generated in the flexure when 10 mN axial and transverse forces are applied at the distal input end of the inner wire of the flexure, respectively. When axial force is applied, the displacement of the proximal output end ($2.8 \times 10^{-5}$ mm) is close to that of the input end. Under transverse force load with the same magnitude, the displacement of the proximal output end is minimized ($3.4 \times 10^{-6}$ mm). By comparison, FEA simulation with the same force loads are performed with the previous flexure design. The displacement generated by axial and transverse forces are $4.4 \times 10^{-4}$ and $5.8 \times 10^{-3}$ mm, respectively. Although the new flexure design does not provide the same large strain amplification under axial force as the previous design, it reduces the crosstalk noise from the transverse force by a factor of 1000.

Fabrication of the 3-DOF Force Sensing Instrument

Figure 3:
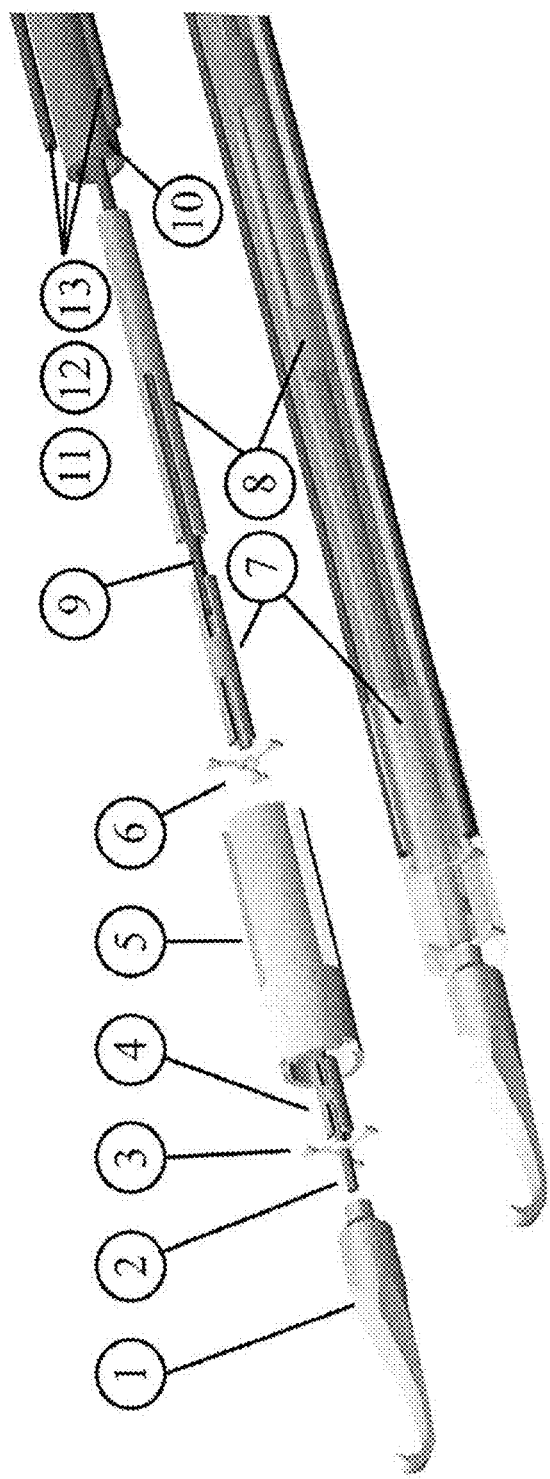
FIG. 3 shows an example of an assembly model of the 3-DOF force sensing instrument according to an embodiment of the current invention. The top is an exploded view and the bottom is a full assembly but with portions being semi-transparent.

The FEA simulation demonstrates that the new flexure design exhibits the desired behaviors of strain amplification for axial force and noise rejection against transverse force. However, its complex structure and small dimensions present challenges for fabrication. An assembly model is devised to fabricate a prototype as a proof of concept. The assembly model consists of components that can be manufactured using photochemical etching and laser micro-machining, as shown in FIG. 3. Two Y-shape beams, 3 and 6, are fabricated with photochemical etching with brass (E-FAB, Santa Clara, Calif.). The stainless steel tubes, 5 and 10, form the main tool shaft. The inner (ID) and outer diameter (OD) of 5 are 0.7 and 0.9 mm, respectively, while 10 has an ID of 0.43 mm and an OD of 0.635 mm. The stainless steel wire 2 (Ø0.125 mm) joins the pick 1, the flexure beams 3 and 6 with the stainless steel tube 4 as spacer between the flexure beams. The stainless steel tube 7 connects the inner wire 2 with distal end of the inner FBG sensor 9. Both 4 and 7 have an ID of 0.15 mm and an OD of 0.31 mm. The proximal side of the inner FBG sensor 9 is fixed by stainless steel tube 8, to align the FBG active segment with the tool axis. The ID and OD of 8 are 0.18 and 0.36 mm, respectively. The outer FBG sensors 11, 12, and 13 are longitudinally attached to the tool shaft 10, with 120° intervals. All stainless steel tubing is laser micromachined (Laserage, Waukegan, Ill.).

Figure 4D:
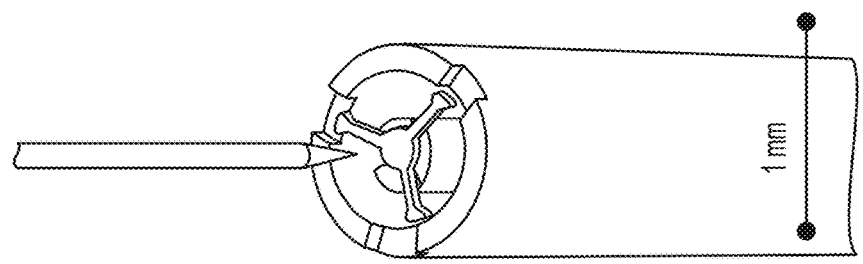
FIGS. 4A-4D show major steps in the assembly process of the flexure (a), (b), (c), and the assembled flexure (d). The assembly is oriented with the tool tip pointing upwards.
Figure 4C:
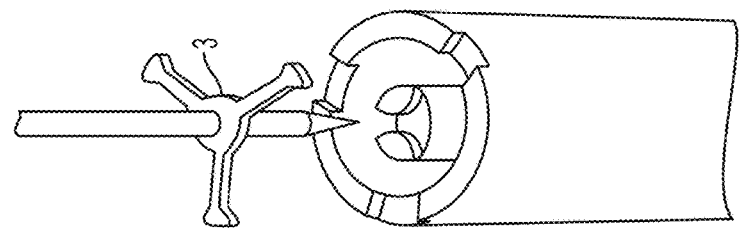
Figure 4B:
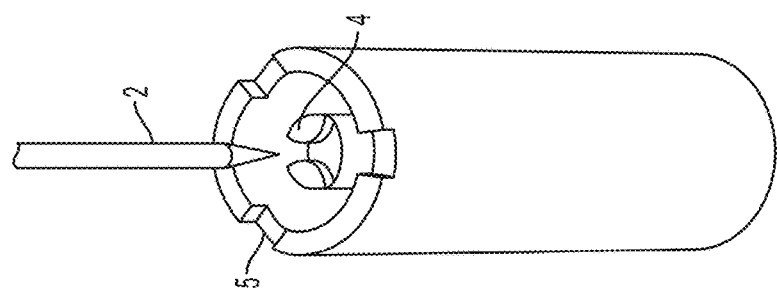
Figure 4A:
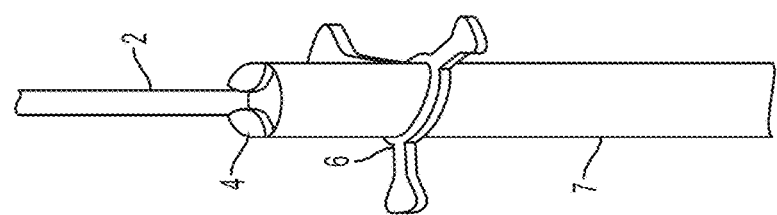

All components are manually assembled under a microscope. FIGS. 4A-4D show the major steps of the flexure assembly process. All connections are adhesive bonded using Loctite 3103 (tensile modulus 207 N/mm², Henkel, CT). First, the center wire 2, spacer 4, flexure beam 6, connector 7, and inner FBG sensor 9 (not shown in FIG. 4A) are connected in series. Second, the outer tube 5 is carefully aligned and joined with the flexure beam 6. Third, the second flexure beam 3 is fixed with the outer tube 5 and spacer 4. FIG. 4D shows the assembled flexure.

Figure 5A:
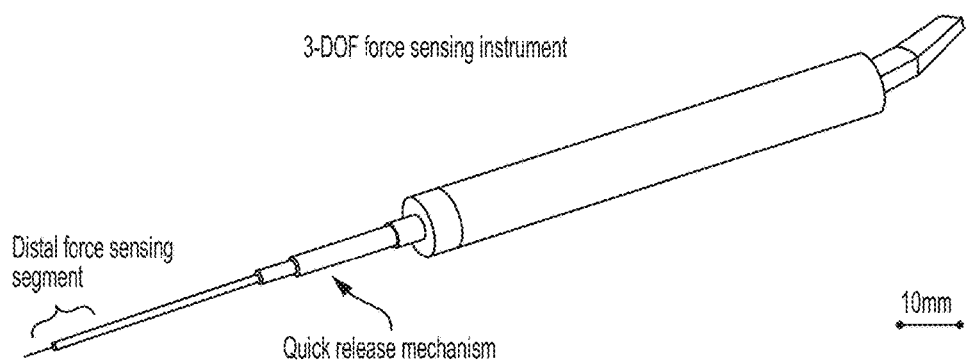
FIGS. 5A-5B show a prototype of the new 3-DOF force sensing instrument (a) according to an embodiment of the current invention. Close-up view of the distal force sensing segment (b).
Figure 5B:
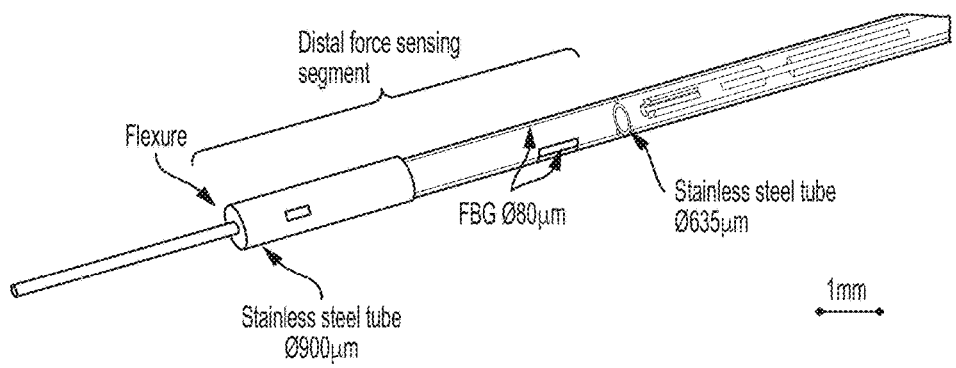

After the flexure is built, the intermediate support tube 8 and the outer tube 10 are added. Subsequently, the outer FBG sensors are attached to outer tube 10. The final step is to install the tool handle with the quick release mechanism. FIGS. 5A-5B illustrate the prototype of the new 3-DOF force sensing instrument according to an embodiment of the current invention. The length of the distal force sensing segment is about 8 mm. Although the micro-pick is not attached in the current prototype, it can be added in the future.

Experiments and Results

Figures 6A, 6B, 6C, 6D:
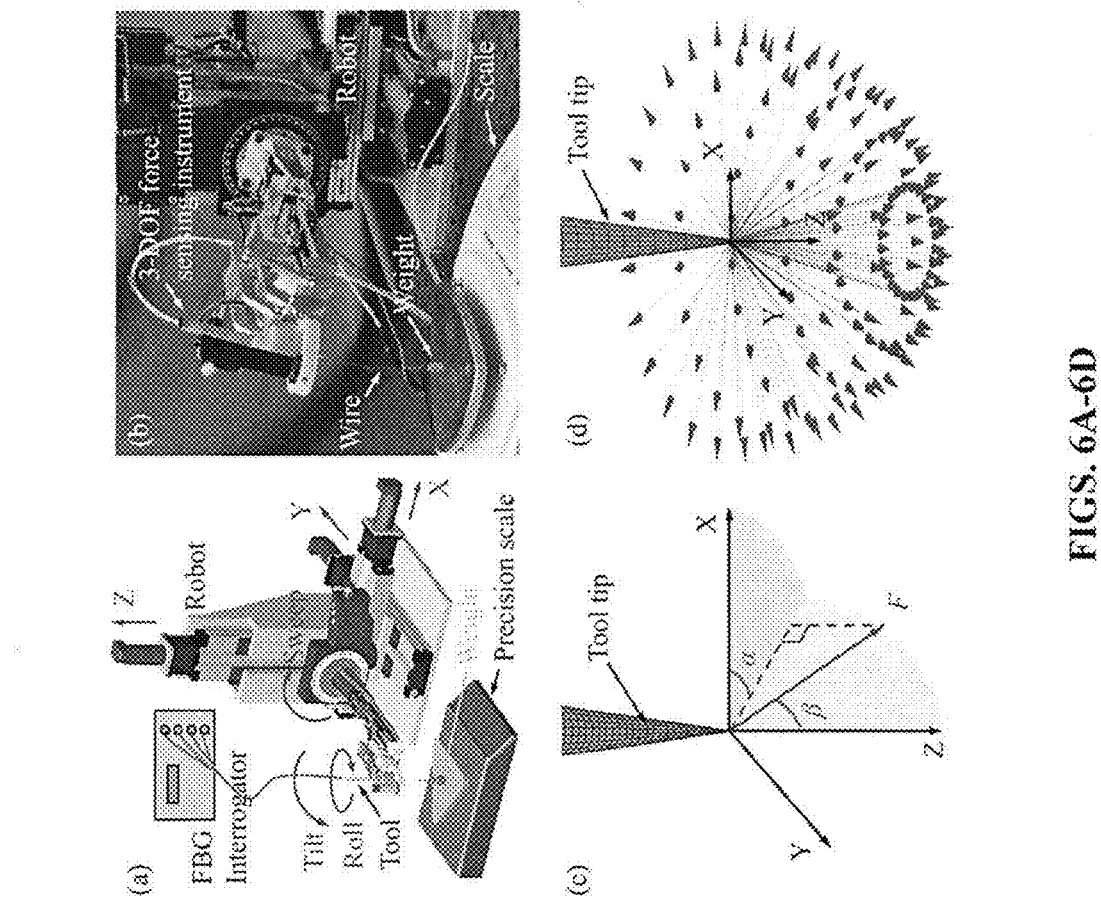
FIGS. 6A-6D a setup of the automated calibration system (a). Close-up view of the actual calibration setup (b). Roll angle $\alpha$ and sweep angle $\beta$ shown in the tool tip coordinate frame (c). All force directions applied in the calibration (d).

The new 3-DOF force sensing instrument is calibrated with an automated calibration system [19]. FIGS. 6A and 6B illustrate the calibration setup. A precision scale is used to measure the force magnitude with 1 mg resolution. A calibration weight (2.15 g) is attached to the tool tip through a thin wire. A high precision robot holds the tool to control its orientation and position. The height of the tool tip with respect to the scale determines the portion of the calibration weight applied on the tool tip, i.e., force magnitude. The two rotational DOFs of the robot, roll and sweep, control the orientation of the tool, thus the direction of the force load. The roll and sweep angles in the tool tip coordinate are illustrated in FIG. 6C. The robot translational and rotational resolution are 1 µm and 0.005°, respectively. The FBG sensors are sampled with an optical sensing interrogator sm130-700 (Micron Optics, Atlanta, Ga.) at 2 kHz refresh rate. More details on the calibration system are described in [19].

The 3-DOF force sensing tool is calibrated in 168 poses with the roll α and sweep β angles varying from −165° to 180°, and from 0° to 90°, respectively, both with 15° incremental. FIG. 6D illustrates all 168 directions of the calibration force loads. At each pose, the force magnitude ranges from 0 to 21 mN. In total, about $2.4 \times 10^5$ calibration samples are obtained. In the following sections, the calibration data is used to determine the mapping from the FBG sensor readings to the transverse and axial forces.

Transverse Force Calibration

Our previous [14], [19] work has shown the FBG sensor readings are linearly dependent on the transverse force. The key equation is shown below for readers' convenience with detailed description in [19]:

$$F_t = K_t \Delta S_t \quad (1)$$

where $F_t = [F_x, F_y]^T$ denotes the transverse force applied at the tool tip, $K_t$ denotes a 2×3 coefficient matrix, and $\Delta S_t = [\Delta s_1, \Delta s_2, \Delta s_3]^T$ is the sensor readings of the three outer FBG sensors.

Figures 7A, 7B, 7C, 7D, 7E, 7F:
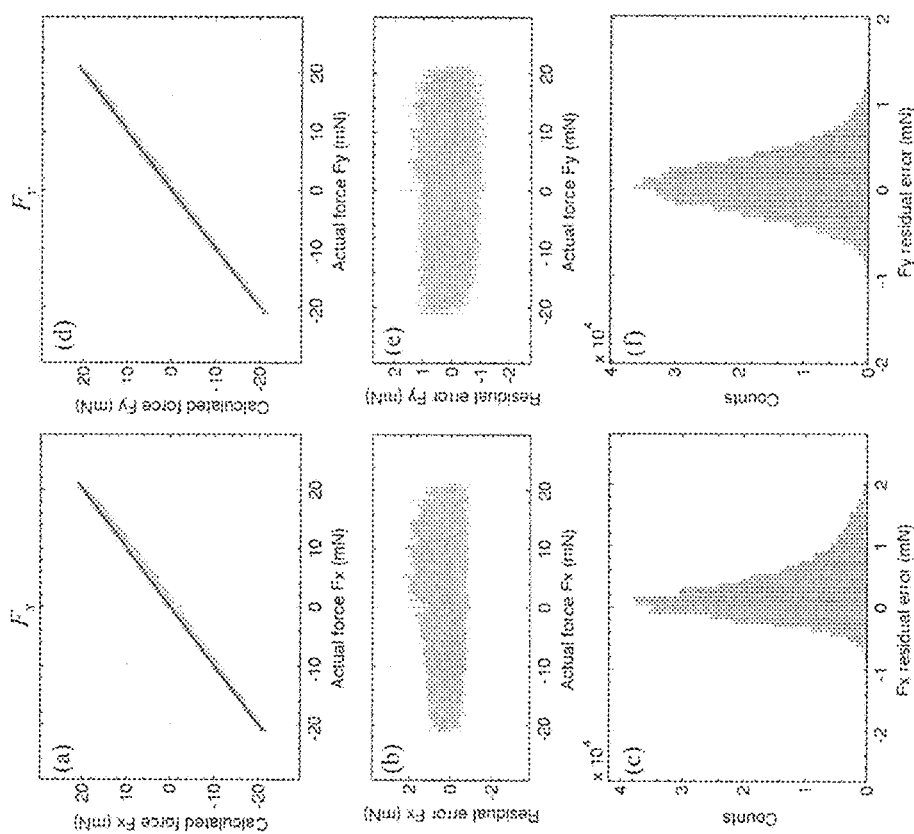
FIGS. 7A-7F show results of transverse force calibration. The calculated Fx versus the actual value using linear fitting (a), the residual error (b), and the histogram of the residual error of Fx (c). Accordingly, (d), (e), and (f) are the same plots for Fy.

FIGS. 7A-7F illustrate the calibration results using linear fitting for transverse force. FIGS. 7A and 7D show the calculated force versus the actual force, in X- and Y-direction, respectively. A straight line through the origin with slope 1 (45°) would be the perfect fit. As shown in FIGS. 7A and 7D, the estimated values of both $F_x$ and $F_y$ are consistent with their actual values. FIGS. 7B and 7E illustrate the residual errors. The root mean square (RMS) error is 0.53 and 0.36 mN for $F_x$ and $F_y$, respectively. FIGS. 7E and 7F show the probability distribution of the residual error.

The distribution of residual error in $F_x$ is skewed to the right, while the distribution of residual error in $F_y$ is fairly symmetric. This could indicate that the manual assembly process, together with machining and assembly tolerance, potentially creates structural asymmetry in the 3-DOF force sensing tool.

Axial Force Calibration

FEA simulation results in above show that the new flexure can be less sensitive for axial force sensing, compared to the previous design, despite improved rejection against crosstalk noise. We first test a linear model, and then use a polynomial model to calculate the axial force.

Figures 8A, 8B, 8C, 8D, 8E, 8F:
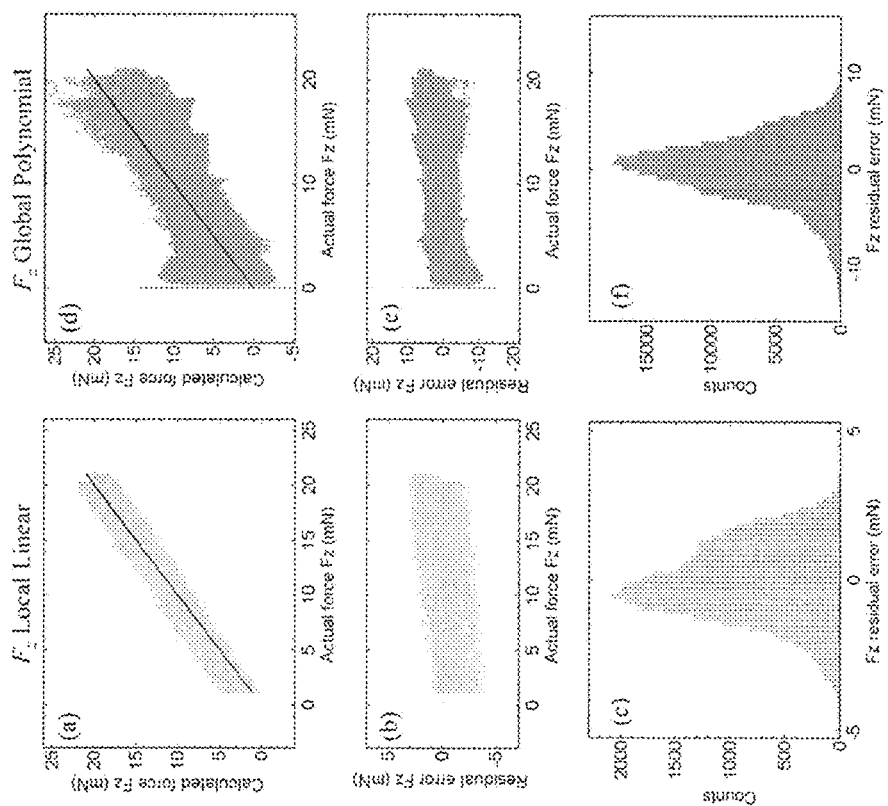
FIGS. 8A-8F show results of axial force calibration. The calculated Fz using linear fitting versus the actual value on the samples with sweep angle $\beta=0$, i.e., pure axial forces (a), the residual error (b), and the histogram of the residual error of Fz (c). Accordingly, (d), (e), and (f) are the same plots for all samples using second-order Bernstein polynomial.

A simple linear model for calculating axial force can be written as:

$$F_z = K_z \Delta \Lambda \quad (2)$$

where $F_z$ denotes the axial force, $K_z$ is a 1×4 coefficient vector, and $\Delta \Lambda = [\Delta\lambda_1, \Delta\lambda_2, \Delta\lambda_3, \Delta\lambda_4]^T$ denotes the Bragg wavelength shifts of the FBG sensors. This linear model provides a local estimate for the samples with the sweep angle β≤15°, as shown in FIGS. 8A, 8B and 8C. This partial data corresponds to all the forces in a cone region with a vertex angle of 30°. The RMS error is 1.27 mN.

A second-order Bernstein polynomial model is used to calculate a global fitting for all calibration data:

$$F_z = \sum_{i=0}^{n}\sum_{j=0}^{n}\sum_{l=0}^{n}\sum_{k=0}^{n} c_{ijlk} b_{i,n} b_{j,n} b_{k,n} b_{l,n} \quad (3)$$

where n=2 is the order of the Bernstein polynomial, Fz denotes the axial force, $c_{ijkl}$ denotes the coefficients, $b_{i,n}(\Delta\lambda^*)$, $b_{j,n}(\Delta\lambda^*)$, $b_{k,n}(\Delta\lambda^*)$, and $b_{l,n}(\Delta\lambda^*)$ are the Bernstein basis polynomials. More detailed description on Bernstein polynomial is in [19].

As shown in FIGS. 8D, 8E and 8F, the polynomial fitting exhibits relatively large error. The RMS error is 3.33 mN, and the maximum residual error is greater than 10 mN. The possible reasons for the large fitting error is discussed below.

Discussion

Behavior of the Inner FBG Sensor

Figure 9A:
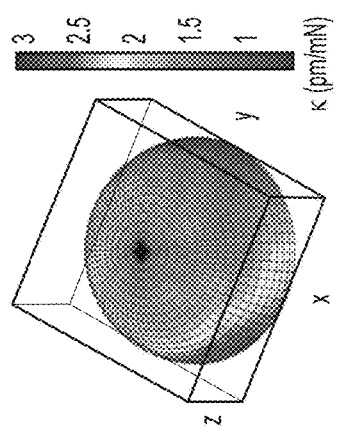
FIGS. 9A-9D show the ratio $\kappa$ between the Bragg wavelength shift of the center FBG $\Delta\lambda_4$ and the force magnitude plotted on the $\alpha$-$\beta$ grid (a), and that plotted on a unit hemisphere (b). Same plots (c) and (d) are generated with the calibration data from previous design.
Figure 9B:
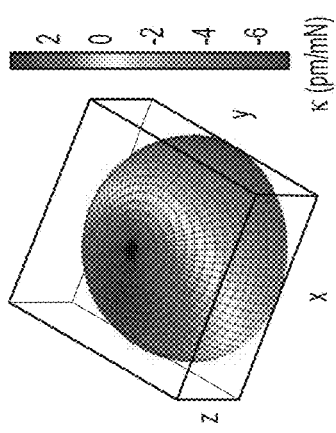

The inner FBG sensor is devoted to measuring the axial force, leveraging strain amplification and noise rejection provided by the flexure design. However, experimental results above indicate that the sensor behavior differs from the design expectation. The Bragg wavelength shift of the inner FBG sensor, $\Delta\lambda_4$, is reviewed carefully with the force loads applied. It is found that $\Delta\lambda_4$ is linearly correlated to the force magnitude in each force direction, i.e., given α and β, $$\Delta\lambda_4 \approx \kappa \|F\| + c \quad (4)$$

where $\|F\|$ is the force magnitude, κ and c denote the slope and the offset of the linear relationship, respectively. The correlation coefficients between $\|F\|$ and $\Delta\lambda_4$ at all 168 poses (combination of 24 roll α and 7 sweep β angles) have a mean of 0.95, with standard deviation of 0.06. The inner FBG sensor exhibits local linearity with respect to the force magnitude. However, the slope κ varies with the force direction, which is determined by α and β. FIGS. 9A and 9B illustrate κ values calculated in each force direction plotted on the α-β grid and on a unit hemisphere, respectively. For better visualization, linear interpolation is used to generate a finer grid/hemisphere with 5° incremental from the original with 15° incremental. First, large variation in κ occurs when β gets close to 90°, i.e., the force load turns toward the transverse direction. This corresponds to the peak and valley along α-axis when β→90°, as shown in FIG. 9A. One possible cause could be that the inner FBG sensor is slightly off the tool axis. Second, although the κ values where α is between 0° and 60° are relatively close, there are still small fluctuations, forming many local humps, as shown in FIG. 9A. This small variation could be due to the non-uniform structural behavior of the miniature, yet complex prototype assembly.

Figure 9C:
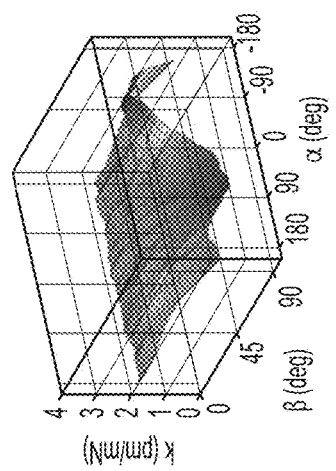
Figure 9D:
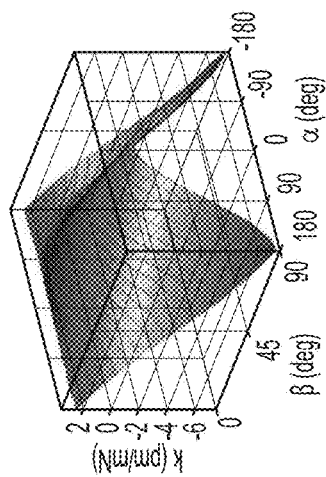

As a comparison, FIGS. 9C and 9D illustrate the κ values calculated using the calibration data of the previous 3-DOF force sensing tool [19]. First, κ presents an even larger shift along α-axis, when β increases to 90°. When the force direction is near transverse, κ can drop below zero. This indicates that the bending due to the transverse force component dominates the tension attributed to the axial force component, resulting in a negative slope between the force magnitude and the Bragg wavelength shift. This observation confirms the drawback of the previous flexure design as mentioned above. As shown in FIG. 9A, the new flexure design improves on suppressing the variation of κ with respect to change of β. Compared to the previous design, it provides a more consistent sensor response as the force direction sweeps between transverse and axial. While the previous design presents the values of κ ranging from −7.2 to 3.3 pm/mN, the κ values of the new design spans from 0.61 to 3.0 pm/mN. This demonstrates the potential of the new flexure to provide improved independent axial force sensing. Second, FIG. 9C shows a smooth variation of κ as the force direction changes, without the humps as shown in FIG. 9A. This could explain why the second-order Bernstein polynomial can provide a good estimate for the previous design, yet is unable to model the fluctuations of the new tool.

Current Issues and Future Improvements

While the FEA simulation predict improvement on decoupled axial force sensing with this new design, the experimental results are difficult to model with a linear or second-order polynomial. Compared with the previous design [19], the new sensor design should provide a refined flexible structure. However, it also presents challenges on fabrication. The assembly model is devised to build a prototype as a proof of concept. In the assembly design, additional assembly tolerances are included when dimensioning the components, in order to allow manual assembly of a dozen of components with micron-level dimensions. More than 20 adhesive bonds are used to join 12 components in a Ø0.9×8 mm volume. The force sensor prototype built is very different from the ideal FEA simulation model. However, the new design of the 3-DOF force sensing instrument does show the potential to achieve better axial force sensing. As shown above, the variation of κ is suppressed into a fairly small interval. Improving the fabrication process would be important to enhance the sensing performance, e.g., reducing noises, and minimizing the peaks and valleys in FIG. 9A. We are considering adopting MEMS techniques to fabricate the flexure as one single part, eliminating the error prone assembly process for the flexure. Design parameters can be optimized according to the MEMS process, in order to improve the axial force sensitivity, as well as to enhance the decoupling and noise rejection. The parameters include width and thickness of the Y-shape flexure beams, as well as the distance between the two sets of the flexure beams.

CONCLUSIONS

Lack of force sensing is one of the most formidable technical challenges in retinal microsurgery. Previous work by our group has investigated 2-DOF and 3-DOF force sensing instruments with fiber optic sensors. Some embodiments of the current invention provide a new 3-DOF force sensing ophthalmic tool with FBG sensors. The force sensing is integrated into the distal portion of the tool shaft with a diameter of 0.9 mm and a length of 8 mm in a particular example. A new flexure is designed to achieve high axial force sensitivity and low crosstalk noise from transverse force. An assembly model is devised to prototype the force sensor. The assembly components are fabricated using photochemical etching and laser micromachining, and manually assembled under microscope. Extensive calibration with force loads up to 21 mN in 168 force directions is carried out using an automated calibration system. Experimental results show that the new 3-DOF force sensing instrument can provide transverse force measurement with 0.5 mN RMS error using a linear model, and axial force measurement with 3.3 mN RMS error using a second-order Bernstein polynomial model. A few observations of the behavior of the inner FBG sensor could provide explanations for the sensing performance of this new tool. They could also suggest possible measures to improve future iterations. As a proof of concept, this new design has demonstrated the potential to enhance independent axial force sensing. To further improve the sensing performance, advanced MEMS techniques can be used to increase the fabrication precision and accuracy.

REFERENCES

[1] P. Gupta, P. Jensen, and E. de Juan, "Surgical forces and tactile perception during retinal microsurgery," in *International Conference on Medical Image Computing and Computer Assisted Intervention*, vol. 1679, 1999, pp. 1218-1225.

[2] A. Menciassi, A. Eisinberg, G. Scalari, C. Anticoli, M. Carrozza, and P. Dario, "Force feedback-based microinstrument for measuring tissue properties and pulse in microsurgery," in *IEEE International Conference on Robotics and Automation*, 2001, pp. 626-631.

[3] J. Peirs, J. Clijnen, D. Reynaerts, H. Van Brussel, P. Herijgers, B. Corteville, and S. Boone, "A micro optical force sensor for force feedback during minimally invasive robotic surgery," *Sensors and Actuators A: Physical*, vol. 115, no. 2-3, pp. 447-455, 2004.

[4] U. Seibold, B. Kubler, and G. Hirzinger, "Prototype of instrument for minimally invasive surgery with 6-axis force sensing capability," in *IEEE International Conference on Robotics and Automation*, 2005, pp. 496-501.

[5] P. Polygerinos, L. D. Seneviratne, R. Razavi, T. Schaeffter, and K. Althoefer, "Triaxial catheter-tip Force sensor for MRI-guided car-diac procedures," *IEEE/ASME Transactions on Mechatronics*, vol. 18, no. 1, pp. 386-396, 2013.

[6] P. Valdastri, K. Harada, A. Menciassi, L. Beccai, C. Stefanini, M. Fu-jie, and P. Dario, "Integration of a miniaturised triaxial force sensor in a minimally invasive surgical tool," *IEEE Transactions on Biomedical Engineering*, vol. 53, no. 11, pp. 2397-2400, 2006.

[7] P. Baki, G. Székely, and G. Kósa, "Miniature tri-axial force sensor for feedback in minimally invasive surgery," in *IEEE International Conference on Biomedical Robotics and Biomechatronics*, 2012, pp. 805-810.

[8] W.-T. Park, R. K. Kotlanka, L. Lou, M. Hamidullah, and C. Lee, "MEMS tri-axial force sensor with an integrated mechanical stopper for guidewire applications," *Microsystem Technologies*, vol. 19, no. 7, pp. 1005-1015, 2012.

[9] P. Baki, G. Székely, and G. Kósa, "Design and characterization of a novel, robust, tri-axial force sensor," *Sensors and Actuators A: Physical*, vol. 192, pp. 101-110, 2013.

[10] B. Bell, S. Stankowski, B. Moser, V. Oliva, C. Stieger, L.-P. Nolte, M. Caversaccio, and S. Weber, "Integrating optical fiber force sensors into microforceps for ORL microsurgery," in *International Conference of the IEEE Engineering in Medicine and Biology Society*, January 2010, pp. 1848-1851.

[11] P. Puangmali, L. D. Seneviratne, P. Dasgupta, and K. Althoefer, "Miniature 3-axis distal Force Sensor for Minimally invasive surgical palpation," *IEEE/ASME Transactions on Mechatronics*, vol. 17, no. 4, pp. 646-656, August 2012.

[12] P. Berkelman, L. Whitcomb, R. Taylor, and P. Jensen, "A miniature instrument tip force sensor for robot/human cooperative microsur-gical manipulation with enhanced force feedback," in *International Conference on Medical Image Computing and Computer Assisted Intervention*, 2000, pp. 247-286.

[13] A. S. Jagtap and C. N. Riviere, "Applied force during vitreoretinal microsurgery with handheld instruments." in *International Conference of the IEEE Engineering in Medicine and Biology Society*, vol. 4, no. 1, January 2004, pp. 2771-2773.

[14] I. Iordachita, Z. Sun, M. Balicki, J. U. Kang, S. J. Phee, J. Handa, P. Gehlbach, and R. Taylor, "A sub-millimetric, 0.25 mN resolution fully integrated fiber-optic force-sensing tool for retinal microsurgery,"

[15] X. He, M. Balicki, J. U. Kang, P. Gehlbach, J. Handa, R. Taylor, and Iordachita, "Force sensing micro-forceps with integrated fiber Bragg grating for vitreoretinal surgery," *SPIE Phontics West*, vol. 8218, no. 82180W, pp. 1-7, 2012.

[16] I. Kuru, B. Gonenc, M. Balicki, J. Handa, P. Gehlbach, R. H. Taylor, and I. Iordachita, "Force sensing micro-forceps for robot assisted retinal surgery." *International Conference of the IEEE Engineering in Medicine and Biology Society*, pp. 1401-1404, January 2012.

[17] X. Liu, I. Iordachita, X. He, R. Taylor, and J. U. Kang, "Miniature fiber-optic force sensor based on low-coherence Fabry-Pérot inter-ferometry for vitreoretinal microsurgery," *Biomedical Optics Express*, vol. 3, no. 5, pp. 1062-1076, May 2012.

[18] B. Gonenc, J. Handa, P. Gehlbach, R. H. Taylor, and I. Iordachita, "Design of 3-DOF force sensing micro-forceps for robot assisted vitre-oretinal surgery," in *International Conference of the IEEE Engineering in Medicine and Biology Society*, vol. 2013, January 2013, pp. 5686-5689.

[19] X. He, J. Handa, P. Gehlbach, R. Taylor, and I. Iordachita, "A sub-millimetric 3-DOF force sensing instrument with integrated fiber Bragg grating for retinal microsurgery." *IEEE Transactions on Biomedical Engineering*, vol. 61, no. 2, pp. 522-534, 2014.

[20] X. He, D. Roppenecker, D. Gierlach, M. Balicki, K. Olds, P. Gehlbach, Handa, R. Taylor, and I. Iordachita, "Toward Clinically Applicable Steady-Hand Eye Robot for Vitreoretinal Surgery," in *ASME 2012 International Mechanical Engineering Congress and Exposition,* 2012, pp. 145-153.

[21] A. Uneri, M. A. Balicki, J. Handa, P. Gehlbach, R. H. Taylor, and I. Iordachita, "New Steady-Hand Eye Robot with micro-force sensing for vitreoretinal surgery," in *IEEE International Conference on Biomedical Robotics and Biomechatronics,* 2010, pp. 814-819.

[22] M. Balicki, A. Uneri, I. Iordachita, J. Handa, P. Gehlbach, and R. Taylor, "Micro-force sensing in robot assisted membrane peeling for vitreoretinal surgery," in *International Conference on Medical Image Computing and Computer Assisted Intervention*, vol. 13, January 2010, pp. 303-310.

[23] X. He, M. Balicki, P. Gehlbach, J. Handa, R. Taylor, and I. Iordachita, "A novel dual force sensing instrument with cooperative robotic assistant for vitreoretinal surgery," in *IEEE International Conference on Robotics and Automation,* 2013, pp. 213-218.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A force-sensing tool, comprising:
a tool shaft comprising a proximal end and a distal end;
a flexure section attached at a first end to said distal end of said tool shaft;
a tool tip operatively connected to said flexure section such that axial forces applied to said tool tip are coupled primarily to a first portion of said flexure section and transverse forces applied to said tool tip are coupled primarily to a second portion of said flexure section;
an axial force sensor coupled to said first portion of said flexure section; and
a transverse force sensor coupled to said second portion of said flexure section,
wherein said first portion of said flexure section is substantially free to move in an axial direction relative to said second portion of said flexure section,
wherein said axial force sensor responds to axial forces applied to said tool tip substantially independently of said transverse forces applied to said tool tip under a designed operating range of forces, and
wherein said transverse force sensor responds to transverse forces applied to said tool tip substantially independently of said axial forces applied to said tool tip under said designed operating range of forces.

2. The force-sensing tool according to claim 1, wherein said axial force sensor comprises an optical fiber that has a Bragg Grating written therein, said optical fiber extending along an inner lumen of said tool shaft such that said first portion of said flexure section and said optical fiber coupled thereto are free to move in an axial direction relative to said second portion of said flexure section.

3. The force-sensing tool according to claim 2, wherein said transverse force sensor comprises a plurality of optical fibers each comprising a Bragg Grating written therein, said plurality of optical fibers extending from said proximal end to said distal end of said tool shaft and being coupled at a distal end to said second portion of said flexure section to become strained in response to transverse forces applied to said tool tip substantially independently of axial forces applied to said tool tip.

4. The force-sensing tool according to claim 3, wherein said plurality of optical fibers are three optical fibers spaced substantially equally spaced around a peripheral portion of said tool shaft.

5. The force-sensing tool according to claim 1, wherein said tool tip is a micro-pick for retinal microsurgery.

6. The force-sensing tool according to claim 1, wherein said tool shaft has a diameter that is a maximum of 0.9 mm.

7. The force-sensing tool according to claim 1, wherein said designed operating range of forces for said transverse force sensor and said axial force sensor is from 0 to 40 mN.

8. The force-sensing tool according to claim 1, wherein a sensing segment of said force-sensing tool comprises said flexure section and said fiber Bragg gratings and has a maximum length less that about 15 mm.

9. A force-sensing tool system, comprising:
a tool force detection system;
a force-sensing tool comprising force sensors configured to communicate with said tool force detection system; and
a processor configured to communicate with said tool force detection system,
wherein said force-sensing tool comprises:
a tool shaft comprising a proximal end and a distal end;
a flexure section attached at a first end to said distal end of said tool shaft;
a tool tip operatively connected to said flexure section such that axial forces applied to said tool tip are coupled primarily to a first portion of said flexure section and transverse forces applied to said tool tip are coupled primarily to a second portion of said flexure section;

an axial force sensor coupled to said first portion of said flexure section; and a transverse force sensor coupled to said second portion of said flexure section, wherein said first portion of said flexure section is substantially free to move in an axial direction relative to said second portion of said flexure section, wherein said axial force sensor responds to axial forces applied to said tool tip substantially independently of said transverse forces applied to said tool tip under a designed operating range of forces, and wherein said transverse force sensor responds to transverse forces applied to said tool tip substantially independently of said axial forces applied to said tool tip under said designed operating range of forces.

10. The force-sensing tool system according to claim 9, further comprising:

a robotic system, said force-sensing tool being attached to said robotic system.

11. The force-sensing tool system according to claim 9, wherein said axial force sensor comprises an optical fiber that has a Bragg Grating written therein, said optical extending along an inner lumen of said tool shaft such that said first portion of said flexure section and said optical fiber coupled thereto are free to move in an axial direction relative to said second portion of said flexure section.

12. The force-sensing tool system according to claim 9, wherein said transverse force sensor comprises a plurality of optical fibers each comprising a Bragg Grating written therein, said plurality of optical fibers extending from said proximal end to said distal end of said tool shaft and being coupled at a distal end to said second portion of said flexure section to become strained in response to transverse forces applied to said tool tip substantially independently of axial forces applied to said tool tip.

13. The force-sensing tool system according to claim 12, wherein said plurality of optical fibers are three optical fibers spaced substantially equally spaced around a peripheral portion of said tool shaft.

14. The force-sensing tool system according to claim 9, wherein said tool tip is a micro-pick for retinal microsurgery.

15. The force-sensing tool system according to claim 9, wherein said tool shaft has a diameter that is a maximum of 0.9 mm.

16. The force-sensing tool system according to claim 9, wherein said designed operating range of forces for said transverse force sensor and said axial force sensor is from 0 to 40 mN.

17. The force-sensing tool system according to claim 9, wherein a sensing segment of said force-sensing tool comprises said flexure section and said fiber Bragg gratings and has a maximum length less that about 15 mm.

* * * * *